United States Patent [19]

Hammond et al.

[11] Patent Number: 5,223,617

[45] Date of Patent: Jun. 29, 1993

[54] PROCESS FOR PRODUCING CHLOROISOCYANURATE COMPOUNDS WITH CONCENTRATED SALT-FREE HYPOCHLOROUS ACID

[75] Inventors: Wayne H. Hammond, Nazareth, Pa.; John H. Shaffer, Cleveland, Tenn.; John A. Wojtowicz, Cheshire, Conn.; Leslie R. Ward, Cleveland, Tenn.; Joseph M. Borcz, Oollewah, Tenn.

[73] Assignee: Olin Corporation, Cheshire, Conn.

[21] Appl. No.: 782,014

[22] Filed: Oct. 24, 1991

[51] Int. Cl.$^5$ .............................................. C07D 25/36
[52] U.S. Cl. .................................................. 544/190
[58] Field of Search .......................... 423/365; 544/190

[56] References Cited

U.S. PATENT DOCUMENTS

| | | | |
|---|---|---|---|
| 3,397,206 | 8/1968 | Nicolaisen | 544/190 |
| 3,668,204 | 6/1972 | Mesiah | 544/190 |
| 3,712,891 | 1/1973 | Berkowitz et al. | |
| 3,803,144 | 4/1974 | Berkowitz | 544/190 |
| 3,806,507 | 4/1974 | Sawhill | 544/190 |
| 3,835,134 | 9/1974 | Schiessl et al. | |
| 3,896,213 | 7/1975 | Hirdler | 544/190 |
| 3,993,649 | 11/1976 | Sawhill et al. | |
| 4,007,182 | 2/1977 | Wojtowicz | |
| 4,024,140 | 5/1977 | Wojtowicz | |
| 4,146,578 | 3/1979 | Brennan et al. | |
| 4,208,519 | 6/1980 | Berkowitz | 544/190 |
| 4,542,218 | 9/1985 | Spooner | 544/190 |

FOREIGN PATENT DOCUMENTS

WO90/05111  5/1990  PCT Int'l Appl.

*Primary Examiner*—Wayne Langel
*Attorney, Agent, or Firm*—F. A. Iskander; James B. Haglind

[57] ABSTRACT

A process for producing a chloroisocyanuric acid compound which comprises reacting cyanuric acid with a chlorinating agent consisting of an aqueous solution of hypochlorous acid substantially free of ionic impurities having a pH of less than about 2. The process produces chloroisocyanuric acid compounds with reduced volumes of effluent solutions and significantly reduced amounts of gas released during operation. The novel process for producing chloroisocyanuric acid compounds can employ solid forms of cyanuric acid as a reactant.

11 Claims, No Drawings

PROCESS FOR PRODUCING CHLOROISOCYANURATE COMPOUNDS WITH CONCENTRATED SALT-FREE HYPOCHLOROUS ACID

BACKGROUND OF THE INVENTION

1. Field of the Invention

This invention relates to a continuous process for producing polychloroisocyanuric acid compounds. Polychloroisocyanuric acid compounds are well known products used in laundry, bleaching and sanitizing applications.

2. Brief Description of the Prior Art

It has long been a desire to produce polychloroisocyanuric acid compounds commercially in a process which eliminates or minimizes the formation of effluents containing both available chlorine as hypochlorite ions and chloride ions. These effluents, which are produced in large volumes, can be re-used to some extent, however, a large portion of the volume of effluent must be treated to convert the available chlorine (hypochlorite ions) to chloride ions by one of several known methods.

In the production of polychloroisocyanuric acids, i.e., dichloroisocyanuric acid and trichloroisocyanuric acid, by the reaction of chlorine with aqueous slurries of alkali metal cyanurates, it is recognized that dilute concentrations of hypochlorous acid, formed in situ, serve as the chlorinating agent. However, in addition, equimolar amounts of hydrochloric acid are produced as a by-product.

The preparation of chloroisocyanuric acids by the reaction of hypochlorous acid with cyanuric acid has been proposed in U.S. Pat. No. 3,712,891 by S. Berkowitz, published Jan. 23, 1973. The patent proposes to react hypochlorous acid solutions having a pH in the range of 3.5–5.0 with cyanuric acid in an aqueous medium at a temperature of 0°–50° C. The process employs dilute solutions of impure hypochlorous acid which result in the formation of large volumes of aqueous effluents containing available chlorine and ionic impurities which have to be used or treated prior to disposal. In addition, operating at pH's above 3 results in reduced reactivity of the hypochlorous acid as well as the release of chlorine-containing gases.

The production of large volumes of dilute solutions containing available chlorine, and usually hydrochloric acid, poses a disposal problem which results in substantial increases in the operating costs for the process. These cost increases are such that they offset the advantages gained by employing dilute hypochlorous acid solutions as a reactant to produce chloroisocyanuric acid solutions which are free of a by-product salt.

Now it has been found that polychloroisocyanuric acids can be produced directly in a single step process without forming a by-product salt and without producing large volumes of dilute effluents containing available chlorine for re-use or disposal.

BRIEF SUMMARY OF THE INVENTION

It is an object of the invention to provide a process for producing a chloroisocyanuric acid compound having reduced volumes of effluent solutions.

An additional object of the present invention is to provide a process for producing a chloroisocyanuric acid compound having significantly reduced amounts of gas released during operation.

Another object of the present invention is to provide a process for producing a chloroisocyanuric acid compound using a single chlorinating agent.

A further object of the present invention is to provide a process for producing a chloroisocyanuric acid compound employing solid forms of cyanuric acid as a reactant.

A still further object of the present invention is to provide a single-step process for producing a chloroisocyanuric acid compound which can be readily controlled.

Yet another object of the present invention is to provide a process for producing a chloroisocyanuric acid compound which can be operated continuously.

These and other advantages are provided in a process for producing a chloroisocyanuric acid compound which comprises reacting cyanuric acid with a chlorinating agent consisting of an aqueous solution of hypochlorous acid substantially free of ionic impurities having a pH of less than about 2.

DETAILED DESCRIPTION OF THE INVENTION

The novel process of the present invention employs as one reactant a concentrated solution of high purity hypochlorous acid, HOCl. The method of producing high purity concentrated HOCl solutions is that in which gaseous mixtures, having high concentrations of hypochlorous acid vapors and chlorine monoxide gas, and controlled amounts of water vapor, are produced, for example, by the process described by J. P. Brennan et al in U.S. Pat. No. 4,147,761. The gaseous mixture is then converted to a concentrated hypochlorous acid solution as described in WO 90/05111 published May 17, 1990 by J. K. Melton, et. al. Each of these publications is incorporated in its entirety by reference.

The concentrated hypochlorous acid solution employed as a reactant contains concentrations in the range of from about 35 to about 60, and more preferably from about 40 to about 55 percent by weight of HOCl. The solution is substantially free of ionic impurities such as chloride ions and alkali metal ions and has low concentrations of dissolved chlorine. For example, concentrations of the chloride ion are preferably less than about 50 parts per million and the alkali metal ion concentration is preferably less than about 50 parts per million. The dissolved chlorine concentration in the hypochlorous acid solution is normally less than about 3 percent, and preferably less than about 1 percent by weight. These highly pure, concentrated solutions of hypochlorous acid are also highly acidic, having a pH of less than about 2, for example, in the range of from about 1 to about 1.75.

Cyanuric acid, the second reactant, is an industrial product which is commercially available. While aqueous slurries of cyanuric acid may be used, it is preferred to limit the amount of water introduced into the process and solid granular cyanuric acid is employed. Solid granular cyanuric acid reactants are exemplified by anhydrous cyanuric acid, cyanuric acid hydrates such as cyanuric acid monohydrate, or mixtures thereof.

In the novel process of the invention, cyanuric acid is admixed with the hypochlorous acid solution, for example, to produce trichloroisocyanuric acid in a reaction represented by the following equation:

$$H_3C_3N_3O_3 + 3HOCl \rightarrow Cl_3C_3N_3O_3 + 3H_2O \tag{1}$$

Where dichloroisocyanuric acid is the desired product, the equation illustrating the reaction is:

$$H_3C_3N_3O_3 + 2HOCl \rightarrow Cl_2HC_3N_3O_3 + 2H_2O \tag{2}$$

An alkali metal salt of dichloroisocyanuric acid can be produced directly by reacting the dichloroisocyanuric acid with an alkali metal hydroxide such as sodium hydroxide in a reaction represented by the following equation:

$$Cl_2HC_3N_3O_3 + NaOH \rightarrow Cl_2NaC_3N_3O_3 + H_2O \tag{3}$$

The process of the present invention is conducted in a reactor preferably by admixing solid particles of cyanuric acid with the hypochlorous acid. As the hypochlorous acid solutions are substantially free of ionic impurities and highly acidic, having a pH below about 2, the reaction mixture of cyanuric acid and the hypochlorous acid releases substantially lower amounts of chlorine containing gases such as chlorine or nitrogen trichloride. Prior art processes using hypochlorous solutions having a pH above 4 contain impurities such as chloride ions which promote the formation of chlorine containing gases thus increasing the operating and safety hazards for these processes. Further, the reactivity of cyanuric acid with hypochlorous acid is improved as the oxidation-reduction potential is increased at the very low pH's present in the process of the invention.

It has been the practice of previous commercial processes to control the reaction mixture and thus the polychloroisocyanuric acid produced, for example, on the basis of the stoichiometric amounts of reactants depicted in Equations (1), (2) and (3). The preparation of the alkali metal cyanurate to be reacted with chlorine was essentially a batch process. Employing the novel process of the present invention in which the highly pure, acidic HOCl solution is used as a reactant, continuous feeding of reactants to the reaction mixture can be employed. Their addition can be accurately controlled, for example, by a combination of the measurements of the oxidation-reduction potential and the pH. The use of this control means is believed to be made possible by the absence in the reaction mixture of substantial amounts of salts such as alkali metal chlorides which, in commercial processes previously used, make accurate determinations of the pH or oxidation-reduction potential difficult. In the present process, where dichloroisocyanuric acid is the desired polychloroisocyanuric acid product, the oxidation-reduction potential of the reaction mixture is maintained in a range of from about $-830$ to about $-870$ millivolts. By maintaining the oxidation-reduction potential in a range of from about $-880$ to about $-930$ millivolts, trichloroisocyanuric acid is produced. At an oxidation-reduction potential in the range of from about $-870$ to about $-880$ millivolts, the product is a mixture of dichloroisocyanuric acid and trichloroisocyanuric acid. Alkali metal salts of dichloroisocyanuric acid are preferably produced by the reaction of dichloroisocyanuric acid with an alkali metal hydroxide where the pH of the reaction mixture is employed as a preferred process control.

This is possible in the process of the invention because of the absence of ionic impurities such as alkali metal chlorides. Where producing, for example, an alkali metal dichloroisocyanurate such as sodium dichloroisocyanurate suitable pH's are in the range of from about 4 to about 6, preferably from about 5 to about 5.5.

Chloroisocyanuric acids produced by the process of slurries. Dichloroisocyanuric acid (DCCA) slurries having concentrations of up to about 55% by weight of DCCA, for example, concentrations in the range of from 40 to about 55%, can be continuously produced. Slurries of alkali metal salts of dichloroisocyanuric acid can be produced having concentrations of up to about 50% by weight, and suitably in the range of from about 30 to about 45%. Trichloroisocyanuric acid (TCCA) slurries are produced containing up to about 50% by weight of TCCA, and preferably with a concentration of from 30 to about 45%. The slurries produced can be fed directly to a dryer such as a spray dryer with no further separating or filtering required as the slurries are free of salt by-products.

The process of the present invention is further illustrated by the following examples. All parts and percentages are by weight unless otherwise specified and temperatures are in degrees Celsius.

EXAMPLE 1

Dry cyanuric acid monohydrate ((200 grams) was added to a 1 liter glass jacketed reactor. Also added to the reactor was an aqueous solution of hypochlorous acid containing 48 percent by weight of HOCl. The hypochlorous acid solution was added at a rate of 1 ml per minute and the reaction mixture formed was maintained at a temperature of 15° C. by circulating coolant through the reactor jacket. During the addition of the hypochlorous acid and the subsequent reaction period the reaction mixture was continuously stirred. The reactor contained an oxidation reduction probe which was referenced to a pH probe and the reaction maintained at a potential of $-835$ millivolts. After a residence time of about 20 minutes, a slurry containing about 54 percent by weight of dichloroisisocyanuric acid (DCCA) overflowed the reactor.

EXAMPLE 2

A portion of the dichloroisocyanuric acid slurry produced by the method of Example 1, containing about 54 percent by weight of DCCA was fed to a 1-liter jacketed glass reactor equipped with a stirrer and oxidation reduction potential probe and a pH probe. An aqueous solution of hypochlorous acid containing 50 percent by weight of HOCl was added to the reactor at a rate of about 1 ml per minute. During the reaction period, the reactor was maintained at a temperature of 15° C. and a potential of $-925$ millivolts. After a residence time of about 40 minutes, a slurry of trichloroisocyanuric acid (TCCA) containing 20 percent by weight of TCCA overflowed the reactor.

EXAMPLE 3

A second portion of the dichloroisocyanuric acid slurry produced by the method of Example 1, containing about 54 percent by weight of DCCA was fed to a 1-liter jacketed glass reactor equipped with a stirrer and oxidation reduction potential probe and a pH probe. A solution of sodium hydroxide containing 50% by weight of 1 NaOH was added to the reactor at a rate of about 1 ml per minute which maintained the pH of the reaction mixture at about 5. During the reaction period, the reactor was maintained at a temperature of 15° C.

After a residence time of about 5 minutes, a slurry of sodium dichloroisocyanurate (SDCC) containing 42 percent by weight of SDCC overflowed the reactor.

What is claimed is:

1. A process for producing a chloroisocyanuric acid compound which comprises reacting cyanuric acid with a chlorinating agent consisting of an aqueous solution of hypochlorous acid substantially free of ionic impurities having a pH of less than about 2 at a concentration of from about 35 to about 60 percent by weight of HOCl.

2. The process of claim 1 accomplished by reacting the cyanuric acid in the form of a particulate solid.

3. The process of claim 1 accomplished by maintaining an oxidation-reduction potential in the range of from about −830 to about −930 millivolts.

4. The process of claim 3 in which the chloroisocyanuric acid compound is dichloroisocyanuric acid, trichloroisocyanuric acid and mixtures thereof.

5. The process of claim 4 in which the chloroisocyanuric acid compound is dichloroisocyanuric acid.

6. The process of claim 5 in which the dichloroisocyanuric acid is reacted with an alkali metal hydroxide at a pH in the range of from about 4 to about 6 to produce an alkali metal dichloroisocyanurate.

7. The process of claim 2 accomplished by reacting cyanuric acid hydrate as the particulate solid.

8. A process for producing a chloroisocyanuric acid compound which comprises reacting solid particles of cyanuric acid with a chlorinating agent consisting of an aqueous solution of hypochlorous acid substantially free of ionic impurities having a pH of less than about 2 at a concentration of from about 35 to about 60 percent by weight of HOCl.

9. The process of claim 8 accomplished by reacting the cyanuric acid as cyanuric acid hydrate.

10. A process for producing an alkali metal dichloroisocyanurate which comprises reacting cyanuric acid with a chlorinating agent consisting of an aqueous solution of hypochlorous acid substantially free of ionic impurities having a pH of less than about 2 at a concentration of from about 35 to about 60 percent by weight of HOCl while maintaining the oxidation-reduction potential in the range of from about −830 to about −880 millivolts to produce dichloroisocyanuric acid, and reacting the dichloroisocyanuric acid with an alkali metal hydroxide to produce an alkali metal dichloroisocyanurate.

11. The process of claim 10 accomplished by maintaining the pH during the reaction of the dichloroisocyanuric acid with the alkali metal hydroxide at from about 4 to about 6.

* * * * *